(12) United States Patent
Leflaive et al.

(10) Patent No.: US 6,838,588 B2
(45) Date of Patent: Jan. 4, 2005

(54) PROCESS FOR CO-PRODUCING PARA-XYLENE AND METAXYLENE, COMPRISING TWO SEPARATION STEPS

(75) Inventors: Philibert Leflaive, Sceaux (FR); Alain Methivier, Orleans (FR); Gérard Hotier, Rueil Malmaison (FR)

(73) Assignee: Institut Francais du Petrole, Rueil Malmaison (FR)

( * ) Notice: Subject to any disclaimer, the term of this patent is extended or adjusted under 35 U.S.C. 154(b) by 454 days.

(21) Appl. No.: 10/108,392

(22) Filed: Mar. 29, 2002

(65) Prior Publication Data

US 2002/0143223 A1 Oct. 3, 2002

(30) Foreign Application Priority Data

Mar. 29, 2001 (FR) .............................. 01 04296

(51) Int. Cl.$^7$ ................................. C07C 7/12
(52) U.S. Cl. ..................... 585/828; 585/822; 585/825; 585/812
(58) Field of Search ................ 585/828, 822, 585/825, 811

(56) References Cited

U.S. PATENT DOCUMENTS 5,284,992 A * 2/1994 Hotier et al. ............... 585/805

FOREIGN PATENT DOCUMENTS

FR          2782714          3/2000

* cited by examiner

*Primary Examiner*—Thuan Dinh Dang
(74) *Attorney, Agent, or Firm*—Millen, White, Zelano & Branigan, P.C.

(57) ABSTRACT

A process is described for co-producing metaxylene and paraxylene from a hydrocarbon feed comprising two separation steps. The first step of the process is a counter-current simulated moving bed system in a chromatographic column containing at least five zones, comprising injecting the feed and injecting a desorbent and delivering an extract, a raffinate and an intermediate raffinate either continuously or discontinuously. The extract is distilled to obtain a paraxylene with a purity of at least 99.7%. The raffinate, which is richer in metaxylene, is distilled to extract the desorbent and injected into a counter-current simulated moving bed continuously delivering an extract and a raffinate. One of these two streams is enriched in metaxylene. The most metaxylene-rich stream is distilled to obtain metaxylene with a purity of more than 99%.

17 Claims, 1 Drawing Sheet

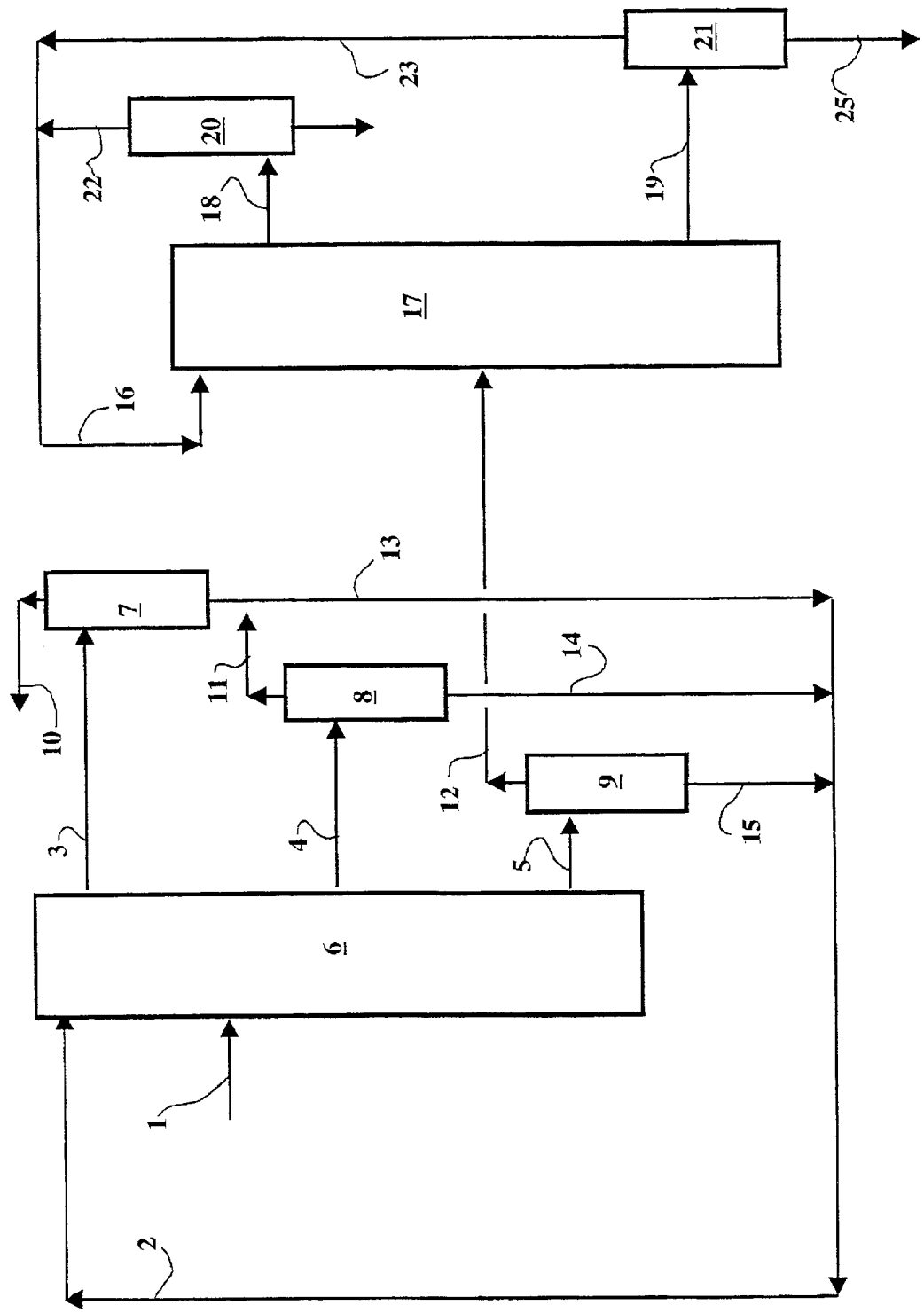

PROCESS FOR CO-PRODUCING PARA-XYLENE AND METAXYLENE, COMPRISING TWO SEPARATION STEPS

The invention relates to a process for co-producing paraxylene and metaxylene from a hydrocarbon feed containing them, the process comprising two separation steps.

The production of high purity paraxylene by adsorption separation is well known in the prior art. This market has developed greatly with the aim of producing terephthalic acid, phthalic anhydride and polyethylene terephthalate resins. In contrast, the metaxylene market is still small, its product being isophthalic acid. However, the prior art is cognisant of processes for producing high purity metaxylene, for example U.S. Pat. Nos. 4,326,092, 5,382,747, and 5,900,523. It has recently been learned that adding small quantities of polyethylene isophthalate to polyethylene terephthalate improves the properties of this latter. Thus, the co-production of paraxylene and metaxylene in the same aromatic production complex is of advantage in satisfying market demands: the quantity of paraxylene must be larger than the quantity of metaxylene: typically 2 to 40 times larger, paraxylene must be very pure, typically at least 99.6% and metaxylene must be of reasonable purity, typically at least 99.0%.

The prior art also describes processes for co-producing paraxylene and metaxylene; for example, U.S. Pat. No. 4,368,347 uses a vapour phase process with a recycle of intermediate fractions: apart from the complication connected with recycling intermediate fractions, this document does not describe and does not suggest how it is possible to carry out such a process in a practical manner operating at a pressure in the range 1 to 2 bars and at a temperature of 150° C. to 200° C. with a feed with a bubble point of 145° C. and with fixed beds with pressure drops of at least 0.1 bar and probably more to function economically. French patent FR-A-2 651 148 uses two different solvents to separate the C8 aromatic cut into three effluents, which severely limits its scope since the number of distillations consecutive to a simulated moving bed separation unit are multiplied. International patent WO-A-93/22022 describes different cases for separating feeds with three constituents into three effluents, however the technology used, involving very high pressures, pressure regulation and regulation of the flow rate in each of three or four zones of the process and the separate beds each in one column, is only economically justified for products with a very high added value.

U.S. Pat. No. 4,306,107 describes a liquid phase simulated moving bed process in which metaxylene is taken off in the form of an extract, paraxylene, orthoxylene and an ethylbenzene fraction are taken off as an intermediate raffinate, and finally ethylbenzene is taken off as a raffinate. Of course, that process of co-producing metaxylene and ethylbenzene cannot enable the co-production of mostly paraxylene accompanied by metaxylene.

U.S. Pat. No. 4,313,015 describes a process for continuous co-production of paraxylene and metaxylene from a hydrocarbon feed in a phase simulated moving bed comprising three withdrawals. The extract is constituted by paraxylene that is too impure (99.44%) to be sold under current standards (current standard=99.7 min) and with a yield of 97.5%; the intermediate raffinate is constituted by ethylbenzene, ortho- and metaxylene and a little paraxylene, and finally the raffinate is principally constituted by a mixture of orthoxylene and metaxylene. Pure metaxylene is then obtained by distilling the raffinate.

A process for continuous co-production of paraxylene and metaxylene from a hydrocarbon feed in a liquid phase simulated moving bed comprising three withdrawals is also described in FR-A-2 782 714. The chromatographic column described contains at least twenty-five beds distributed over five zones. At least five beds must be located in zone 3B comprised between the point for taking off an intermediate raffinate containing metaxylene, orthoxylene, ethylbenzene, solvent and paraxylene and the point for taking off a raffinate containing metaxylene, orthoxylene and solvent. Metaxylene with a purity of more than 99% is then obtained by distilling raffinate. Apart from the large number of beds required to carry out the process (30, for example), the hydrocarbon feed has an ethylbenzene content of less than 5%, which is restricting.

The Applicant has filed a French patent application, FR-A-2 808 270, which describes a process for co-production in a simulated moving bed of paraxylene and metaxylene in a chromatographic column comprising three withdrawals from a feed that is not limited in ethylbenzene, in which an extract containing paraxylene is taken off continuously, the first raffinate is taken off continuously or discontinuously and in which the second raffinate comprising orthoxylene and metaxylene is withdrawn discontinuously, the process also being characterized in that the second raffinate is distilled to recover orthoxylene and metaxylene with a purity of at least 99%.

U.S. Pat. No. 5,510,562 also describes a process for separating C8 aromatics in which a mixture of orthoxylene, metaxylene, paraxylene and ethylbenzene is firstly divided into two streams respectively containing paraxylene and ethylbenzene, and metaxylene and orthoxylene. The paraxylene is then separated from the ethylbenzene by distillation followed by crystallisation, and metaxylene is separated from the orthoxylene by distillation.

In all of the processes described in patents U.S. Pat. No. 4,313,015, FR-A-2 782 714 and U.S. Pat. No. 5,510,562 and in patent application application FR-A-2 808 270metaxylene is seperated from orthoxylene by distillation. Now, the boiling points of these two compounds are very close together (i.e., respectively 139.12 and 144.41 ), which renders separation of these two compounds by distillation very difficult and necessitates a large column with at least about 150 to 200 plates. Further, if the stream of the metaxylene and orthoxylene mixture which is to be separated contains paraxylene and ethylbenzene as impurities, these impurities will become concentrated in the metaxylene, rendering a purity of more than 99.0% difficult.

The prior art document that is closest to the invention is U.S. Pat. No. 5,900,523 . Example E of that document describes a process for producing xylenes in which a first separation zone by paraselective adsorption produces an extract that is enriched in paraxylene and a raffinate that comprises at least the majority of the orthoxylene and metaxylene present in the supply stream and which contains more than 10% of orthoxylene. The extract is distilled to recover high purity paraxylene. The raffinate from the first separation zone is then introduced into a second metaselective adsorption zone where the adsorbent is a Y zeolite with an $SiO_2/Al_2O_3$ mole ratio in the range 4.0 to 6.0 exchanged with sodium and with a water content equivalent to an LOI at 500° C. of about 1.5% to about 2.5% by weight and where separation is carried out in the liquid phase at a temperature in the range 100° C. to 150° C. The second zone for separation by metaselective The invention concerns the co-production of commercialisable paraxylene and metaxylene from a hydrocarbon feed. In a second aspect, the invention concerns producing paraxylene with a purity of at least 99.6% (with a minimum yield of 98%) and metaxylene with a purity of at least 99% after distillation. In a third aspect, the invention concerns producing paraxylene and metaxylene with two separation units wherein the size of the second unit is reduced.

More precisely, the invention concerns a process for co-producing paraxylene and metaxylene from a hydrocarbon feed comprising them, the process comprising a first step for separating the feed in a simulated moving bed in at least a first chromatographic column (6) containing a plurality of beds of at least one adsorbent interconnected into a loop, said cm comprising a feed injection (1), a take-off for a first raffinate (4), a take-off for a second raffinate (5) comprising a desorbent, and a mixture containing metaxylene and orthoxylene that is substantially free of ethylbenzene and paraxylene, an injection point for desorbent (2) and a take-off for an extract delivering very high purity paraxylene, the process comprising periodic simultaneous shifting of the feed and desorbent injection positions and for the extract take-off position by one bed in the direction of flow of a principal stream moving in said first column (6), the process being characterized in that the second raffinate is distilled to eliminate the desorbent, a mixture (12) containing metaxylene and orthoxylene is recovered, a second step for separating at least a portion of the mixture of orthoxylene and metaxylene is carried out in at least one second chromatographic column (17) containing at least one adsorbent and comprising at least one point for injection of the mixture (12), an injection point for a desorbent (16), a take-off for an extract (18) containing desorbent and enriched in the component that is the most adsorbed on the adsorbent, and a take-off for a raffinate (19) containing desorbent and enriched in the compound that is the least adsorbed on the adsorbent, the process being further characterized in that the extract containing metaxylene or the raffinate containing metaxylene is distilled to eliminate desorbent and recover metaxylene with a purity of more than 99%.

The second separation step can be carried out batchwise. It can also be carried out continuously depending on the simulated moving bed technique, preferably with a counter-current simulated moving bed. To this end, the positions for injecting the mixture and desorbent and the positions for taking, off the extract and raffinate are periodically and simultaneously shifted relative to the second chromatographic column by one bed in the direction of flow of a principal stream moving in said second column.

The advantages of the process of the invention over the prior art are as follows:

metaxylene is not separated from orthoxylene by distillation, which is difficult and expensive;

for a given production and for metaxylene isopurity, the dimensions of the columns for the second adsorption step are reduced with respect to those necessitated by the prior art, for example 10% to 20% smaller;

paraxylene and metaxylene can be produced with no severe constraint on the number of beds of adsorbent and on the ethylbenzene content of the feed.

During the first simulated moving bed separation step, the first and second raffinate can be taken off continuously or discontinuously. By taking off the second raffinate, preferably continuously, it can be injected continuously into the distillation step, without an intermediate buffer reservoir.

In accordance with a characteristic of the process, the adsorbent used in the first separation step can comprise an X zeolite exchanged with barium or a Y zeolite exchanged with potassium or a Y zeolite exchanged with barium and potassium.

The preferred desorbent is para-diethylbenzene, however other desorbents such as toluene, para-difluorobenzene or diethylbenzenes as a mixture are also suitable. Preferably, para-diethylbenzene is used because it is easy to recover by distillation and it has a strong affinity for the adsorbent.

In accordance with a further characteristic of the process, it is possible to use a metaselective adsorbent in the second step for separating orthoxylene and metaxylene compounds from the second raffinate. In this case, the extract taken off contains desorbent and substantially pure metaxylene, the compound that is the most adsorbed. However, it is also possible to use an adsorbent in which the raffinate delivers substantially pure metaxylene and in which the extract delivers orthoxylene, in solution in the desorbent with the remaining impurities.

The preferred desorbent for the second separation step is toluene, however other desorbents such as indane, 1,2,4-trimethylbenzene, para-methyl ethylbenzene or cumene, used pure or as a mixture, may also be suitable.

The adsorbent for the second separation stage can comprise at least one zeolite selected from the group essentially formed by an X zeolite exchanged with calcium, an X zeolite exchanged with caesium, a Y zeolite exchanged with sodium or a Y zeolite exchanged with sodium and lithium. Preferably, the use of a Y zeolite containing substantially no sodium is used. Examples of metaselective zeolites containing sodium are described in U.S. Pat. Nos. 4,326,092, 5,382,747, 5,900,523 and European patent EP-A-0 712 821.

In accordance with a further characteristic of the invention, the volume ratio of the desorbent to the feed in the first separation step can be in the range 0.5 to 2.5, preferably in the range 1to 2.

In a further characteristic of the invention, each of the steps of the process can be operated at a temperature that is generally in the range 20° C. to 250° C., preferably in the range 90° C. to 210° C., more particularly in the range 160° C. to 200° C., and at a pressure in the rang from atmospheric pressure to 20 bars (1 bar=0.1 MPa).

The invention will be better understood from the accompanying figure that illustrates the co-production of paraxylene and metaxylene in a counter-current simulated moving bed.

A feed of xylenes comprising metaxylene, orthoxylene, ethylbenzene and paraxylene is continuously introduced via a line (1) into at least one chromatographic column (6) with at least five zones containing a plurality of beds of an adsorbent comprising a zeolite, an X zeolite exchanged with barium, for example, and operating in a liquid phase in a counter-current simulated moving bed in accordance with U.S. Pat. No. 4,313,015 and the Applicant's patent cited above. A first raffinate R1 is continuously taken off via a line (4) at a point located downstream of the feed introduction point, while a second raffinate R2 containing metaxylene and orthoxylene is continuously taken off via a line (5) downstream of the first raffinate with respect to the direction of flow of fluids in a column (specifically, from bottom to top). A desorbent, para-diethylbenzene, is continuously injected via a line (2) at a point in the column located upstream of the feed injection point, while an extract containing desorbent and substantially pure paraxylene is continuously extracted via a line (3) at a point located downstream of the desorbent injection point. This extract is distilled in a distillation column (7), from which substantially pure paraxylene (more than 99.7%) is taken off via a line (10) and desorbent is taken off via a line (13), which may be recycled.

The first raffinate is introduced into a distillation column (8) from which the desorbent is taken off from the bottom via a line (14), which can be recycled, and overhead, a mixture containing xylenes and ethylbenzene is taken off via a line (11). This mixture can be sent to an isomerisation unit.

The second raffinate is introduced into a distillation column (9) from which desorbent is taken off from the bottom via a line (15), which can be recycled, and overhead, a mixture containing essentially metaxylene and orthoxylene and substantially free of paraxylene and ethylbenzene is taken off via a line (12). This line (12) is connected to the inlet to at least one second chromatographic column (17) comprising a plurality of beds of a zeolitic adsorbent, for example a NaY zeolite, which is operated in the liquid phase in a counter-current simulated moving bed, for example as described in U.S. Pat. No. 4,326,092 or U.S. Pat. No. 5,382,747, with a Y zeolite containing sodium.

A desorbent, for example toluene, is continuously introduced via a line (16) into the chromatographic column (17) at a point located upstream of the feed introduction point, while an extract containing substantially pure metaxylene and desorbent is continuously taken off via a line (18) downstream of the point for introducing desorbent and upstream of the feed introduction point. Take-off line (18) is connected to the inlet to a distillation column (20) from which the desorbent is taken off via an overhead line (22) in conventional manner, while metaxylene with a purity of more than 99%, for example, is recovered from the bottom via a line (24).

Downstream of the point for injecting said feed in the direction of flow of the principal fluid moving in the column, a raffinate containing orthoxylene, impurities and desorbent is continuously taken off via line (19) and distilled in a distillation column (21). Orthoxylene containing impurities is recovered from the bottom of column (21) via a line (25) and can optionally be isomerised with that of line 11, while the desorbent is recovered from the head of the column (21) via a line (23).

The points for introducing feed and desorbent and the points for taking off extract and raffinate are periodically and simultaneously shifted in the direction of the flow of the fluid moving in the columns.

The invention is illustrated in the following non limiting examples.

EXAMPLE 1 COMPARATIVE

Paraxylene was produced from a feed comprising a mixture of xylenes and ethylbenzene with the following composition by weight:
PX: paraxylene, 22.6%;
MX: metaxylene, 49.9%
OX: orthoxylene, 21.9%
EB: ethylbenzene,
5.6% in a simulated moving bed with 4 zones, as a counter-current in two cylindrical adsorbers with a 1 m² cross section composed of 24 beds containing a barium-exchanged X zeolite.

The operating conditions were as follows:
feed: 9.5 m$^3$.h$^{-1}$;
solvent: 16.2 m$^3$.h$^{-1}$ of para-diethylbenzene;
extract: 9.6 m$^3$.h$^{-1}$;
raffinate: 16.1 m$^3$ .h$^{-1}$;
recycle rate (to zone 1): 48.2 m$^3$.h$^{-1}$.

The configuration was 5 beds, 9 beds, 8 beds and 2 beds respectively in zones 1, 2, 3 and 4.

The valve permutation time (period) was 70.8 seconds.

After distilling the para-diethylbenzene, the extract obtained delivered 99.7% pure paraxylene in a yield of 96.7%.

The 16.1 m$^3$.h$^{-1}$ of raffinate was distilled and a flow rate of 7.4 m$^3$.h$^{-1}$ of fluid was obtained with the following composition:
PX: paraxylene, 1.0%;
MX: metaxylene, 63.8%;
OX: orthoxylene, 28.0%;
EB: ethylbenzene, 7.2%

A portion, i.e., 0.642 m$^3$.h$^{-1}$ of this fluid was removed and sent to a metaselective separation unit. Metaxylene was produced in a counter-current simulated moving bed in two cylindrical adsorbers with a cross section of 0.0803 m² composed of 24 beds containing a sodium-exchanged Y zeolite.

The operating conditions were as follows:
feed: 0.642 m$^3$.h$^{-1}$ ;
solvent: 1.027 m$^3$.h$^{-1}$ of toluene;
extract: 0.757 m$^3$.h$^{-1}$;
raffinate: 0.912 m$^3$ .h$^{-1}$;
recycle flow rate (to zone 1 ): 4.045 m$^3$.h$^{-1}$ The configuration was 3 beds, 11 beds, 7 beds and 3 beds respectively in zones 1, 2, 3 and4.

The valve permutation time (period) was 90 seconds.

After distilling the toluene, the extract obtained delivered 0.208 m$^3$.h$^{-1}$ of 99.03% pure metaxylene. Paraxylene production was 10 times higher than that of metaxylene.

EXAMPLE 2

Paraxylene was produced from a feed comprising a mixture of xylene and ethylbenzene with the following composition by weight:
PX: paraxylene, 22.6%;
MX: metaxylene, 49.9%
OX: orthoxylene, 21.9%
EB: ethylbenzene, 5.6%
in a simulated moving bed with five zones, as a counter-current in two cylindrical adsorbers with a 1 m² cross section composed of 24 beds containing a barium-exchanged X zeolite. A raffinate (raffinate 2) and an intermediate raffinate were taken off continuously.

The operating conditions were as follows:
feed: 9.5 m$^3$.h$^{-1}$;
solvent: 16.2 m$^3$.h$^{-1}$ of para-diethylbenzene;
extract: 9.6 m$^3$.h$^{-1}$;
intermediate raffinate: 10.1 m$^3$.h$^{-1}$;
raffinate 2: 6.0 m$^3$.h$^{-1}$;
recycle rate (to zone 1): 48.2 m$^3$.h$^{-1}$.

The configuration was 5 beds, 9 beds, 5 beds, 3 beds and 2 beds respectively in zones 1, 2, 3A, 3B and 4.

The valve permutation time (period) was 70.8 seconds.

After distilling the para-diethylbenzene, the extract obtained delivered 99.7% pure paraxylene in a yield of 96.7%. It can be seen that doubling the raffinate did not degrade the performance of the unit for paraxylene production.

The 6.0 m$^3$.h$^{-1}$ of raffinate 2 was distilled and a flow rate of 1.13 m$^3$.h$^{-1}$ of fluid was obtained with the following composition:
PX: paraxylene, 0.7%;
MX: metaxylene, 71.7%;
OX: orthoxylene, 27.5%;
EB: ethylbenzene, 0.1%

A portion, i.e., 0.580 m$^3$.h$^{-1}$ of this fluid was removed and sent to a metaselective separation unit. Metaxylene was produced in a counter-current simulated moving bed in two cylindrical adsorbers with a cross section of 0.0725 m$^2$ composed of 24 beds containing a sodium-exchanged Y zeolite.

The operating conditions (flow rates) were as follows:
feed: 0.580 m$^3$.h$^{-1}$;
solvent: 0.928 m$^3$.h$^{-1}$ of toluene;
extract: 0.675 m$^3$.h$^{-1}$;
raffinate: 0.833 m$^3$.h$^{-1}$;
recycle flow rate (to zone 1): 3.930 m$^3$.h$^{-1}$ The configuration was 3 beds, 11 beds, 8 beds and 2 beds respectively in zones 1, 2, 3 and 4.

The valve permutation time (period) was 82 seconds.

After distilling the toluene, the extract obtained delivered 0.208 m$^3$.h$^{-1}$ of 99.04% pure metaxylene, i.e., a paraxylene production that was ten times higher than that of metaxylene.

In this example, it can be seen that the first unit was operated with a limited number of beds, 24. Further, the quantities of adsorbent and solvent required in the second simulated moving bed adsorption unit for a production of metaxylene that was identical was about 10% lower than that for Example 1.

EXAMPLE 3

Paraxylene was produced from a feed that was richer in ethylbenzene than that of Example 2 and comprising a mixture of xylenes and ethylbenzene with the following composition by weight:
PX: paraxylene, 21.1%;
MX: metaxylene, 48.9%
OX: orthoxylene, 21.4%
EB: ethylbenzene, 8.6%

In a counter-current simulated moving bed in two cylindrical adsorbers with a 1 m$^2$ cross section composed of 24 beds containing a barium-exchanged X zeolite. A raffinate (raffinate 2) and an intermediate raffinate were taken off continuously.

The operating conditions were as follows:
feed: 9.5 m$^3$.h$^{-1}$;
solvent: 16.2 m$^3$.h$^{-1}$ of para-diethylbenzene;
extract: 9.5m$^3$.h$^{-1}$;
intermediate raffinate: 12.05 m$^3$.h$^{-1}$;
raffinate 2: 4.15 m$^3$.h$^{-1}$;
recycle rate (to zone 1): 48.2 m$^3$.h$^{-1}$.

The configuration was 5 beds, 9 beds, 5 beds, 3 beds and 2 beds respectively in zones 1,2,3 A,3 B and 4.

The valve permutation time (period) was 70.8 seconds.

After distilling the para-diethylbenzene, the extract obtained delivered 99.7% pure paraxylene in a yield of 96.0%.

The 4.15 m$^3$.h$^{-1}$ of raffinate 2 was distilled and a flow rate of 0.62 m$^3$.h$^{-1}$ of fluid was obtained with the following composition:
PX: paraxylene, 1.4%;
MX: metaxylene, 70.2%;
OX: orthoxylene, 28.2%;
EB: ethylbenzene, 0.2%

A portion, i.e., 0.595 m$^3$.h$^{-1}$ of this fluid was taken off and sent to a metaselective separation unit. Metaxylene was produced in a counter-current simulated moving bed in two cylindrical adsorbers with a cross section of 0.0745 m$^2$ composed of 24 beds containing a sodium-exchanged Y zeolite.

The operating conditions (flow rates) were as follows:
feed: 0.595 m$^3$.h$^{-1}$;
solvent: 0.952 m$^3$.h$^{-1}$ of toluene;
extract: 0.684 m$^3$.h$^{-1}$;
raffinate: 0.863 m$^3$.h$^{-1}$;
recycle flow rate (to zone 1): 4.028 m$^3$.h$^{-1}$ The configuration was 3 beds, 11 beds, 8 beds and 2 beds respectively in zones 1, 2, 3 and 4.

The valve permutation time (period) was 82 seconds.

After distilling the toluene, the extract obtained delivered 0.208 m$^3$.h$^{-1}$ of 99.05% pure metaxylene, i.e., a paraxylene production that was ten times higher than that of metaxylene.

What is claimed is:

1. A process for co-producing paraxylene and metaxylene from a hydrocarbon feed comprising them, the process comprising a first step for separating the feed in a simulated moving bed in at least a first chromatographic column (6) containing a plurality of beds of at least one adsorbent interconnected into a loop, said column comprising a feed injection (1), a take-off for a first raffinate (4), a take-off for a second raffinate (5) comprising a desorbent, and a mixture containing metaxylene and orthoxylene that is substantially free of ethylbenzene and paraxylene, an injection point for desorbent (2) and a take-off for an extract delivering very high purity paraxylene, the process comprising periodic simultaneous shifting of the feed and desorbent injection positions and for the extract take-off position by one bed in the direction of flow of a principal stream moving in said first column (6), the process being characterized in that the second raffinate is distilled to eliminate the desorbent, a mixture (12) containing metaxylene and orthoxylene is recovered, a second step for separating at least a portion of the mixture of orthoxylene and metaxylene is carried out in at least one second chromatographic column (17) containing at least one adsorbent and comprising at least one point for injection of the mixture (12), an injection point for a desorbent (16), a take-off for an extract (18) containing desorbent and enriched in the component that is the most adsorbed on the adsorbent, and a takeoff for a raffinate (19) containing desorbent and enriched in the compound that is the least adsorbed on the adsorbent, the process being further characterized in that the extract containing metaxylene or the raffinate containing metaxylene is distilled to eliminate desorbent and recover metaxylene with a purity of more than 99%.

2. A process according to claim 1, in which the second separation step is carried out in a simulated moving bed.

3. A process according to claim 1, in which the adsorbent for the second separation step is metaselective and in which the extract contains substantially pure metaxylene.

4. A process according to claim 1, in which the first and second raffinate are taken off continuously, during the first separation step.

5. A process according to claim 1, in which the desorbent for the first separation step is para-diethylbenzene.

6. A process according to claim 1, in which the adsorbent for the first separation step comprises a barium-exchanged X zeolite, a potassium-exchanged Y zeolite or a barium- and potassium-exchanged Y zeolite.

7. A process according to claim 1, in which the desorbent for the second separation step is toluene or indane.

8. A process according to claim 1, in which the adsorbent for the second separation step comprises a Y zeolite containing sodium or a Y zeolite containing sodium and lithium.

9. A process according to claim 1, in which the ratio of desorbent to feed in the first and second separation steps is in the range 0.5 to 2.5.

10. A process according to any one of claim 1, in which the temperature of the adsorption steps is in the range 20° C. to 250° C. at a pressure of 1 bar to 20 bars.

11. A process according to claim 5, in which the adsorbent for the first separation step comprises a barium-exchanged X zeolite, a potassium-exchanged Y zeolite or a barium- and potassium-exchanged Y zeolite.

12. A process according to claim 6, in which the desorbent for the second separation step is toluene or indane.

13. A process according to claim 6, in which the adsorbent for the second separation step comprises a Y zeolite containing sodium or a Y zeolite containing sodium and lithium.

14. A process according to claim 7, in which the adsorbent for the second separation step comprises a Y zeolite containing sodium or a Y zeolite containing sodium and lithium.

15. A process according to claim 12, in which the adsorbent for the second separation step comprises a Y zeolite containing sodium or a Y zeolite containing sodium and lithium.

16. A process according to claim 15, in which the ratio of desorbent to feed in the first and second separation steps is in the range of 0.5 to 2.5.

17. A process according to claim 16, wherein the ratio is in the range of 1 to 2.

* * * * *

UNITED STATES PATENT AND TRADEMARK OFFICE
CERTIFICATE OF CORRECTION

PATENT NO.    : 6,838,588 B2
DATED         : January 4, 2005
INVENTOR(S)   : Philibert Leflaive et al.

It is certified that error appears in the above-identified patent and that said Letters Patent is hereby corrected as shown below:

Column 8,
Line 45, "takeoff" should be -- take-off --.

Column 9,
Line 7, "to any one of claim 1" should be -- claim 1 --.

Signed and Sealed this

Tenth Day of May, 2005

JON W. DUDAS
*Director of the United States Patent and Trademark Office*